United States Patent [19]

Sugiya et al.

[11] Patent Number: 5,679,849

[45] Date of Patent: Oct. 21, 1997

[54] METHOD OF PRODUCING A BIS(2-CARBOXYETHYL)ALKYL PHOSPHINE OXIDE AND A DERIVATIVE THEREOF

[75] Inventors: Masashi Sugiya; Tsutomu Watanabe; Kaoru Takeuchi, all of Tokyo, Japan

[73] Assignee: Nippon Chemical Industrial Co., Ltd., Tokyo, Japan

[21] Appl. No.: 587,529

[22] Filed: Jan. 17, 1996

[30] Foreign Application Priority Data

Jan. 20, 1995 [JP] Japan ................................ 7-007464

[51] Int. Cl.$^6$ ................................................ C07C 55/00
[52] U.S. Cl. ....................... 562/594; 558/385; 568/14; 987/110; 987/125; 987/134
[58] Field of Search ............................ 562/594; 568/14; 528/337, 310; 558/385; 987/110, 125, 134

[56] References Cited

U.S. PATENT DOCUMENTS 4,149,014  4/1979  Wilson .................................... 562/594
4,537,993  8/1985  Savides et al. ........................... 568/14

*Primary Examiner*—Terressa Mosley
*Attorney, Agent, or Firm*—Oblon, Spivak, McClelland, Maier & Neustadt, P.C.

[57] ABSTRACT

A method of producing a bis(2-carboxyethyl)-alkyl phosphine oxide represented by the following general formula (1) is disclosed.

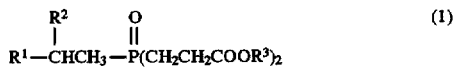

The method comprises the following Steps 1–4: step 1 wherein phosphine is reacted with acrylonitrile to produce bis(2-cyanoethyl)phosphine and then, in step 2, reacted with an alkene to produce a bis(2-cyanoethyl)alkyl phosphine, and in step 3, reacted with an oxidizing agent to produce a bis(2-cyanoethyl)alkyl phosphine oxide, and in step 4, said bis(2-cyanoethyl)alkyl phosphine oxide is reacted with water or a lower alcohol to give a bis(2-carboxyethyl)alkyl phosphine oxide or a derivative thereof.

9 Claims, No Drawings

METHOD OF PRODUCING A BIS(2-CARBOXYETHYL)ALKYL PHOSPHINE OXIDE AND A DERIVATIVE THEREOF

BACKGROUND OF THE INVENTION

The present invention relates to a method of producing a bis(2-carboxyethyl)alkyl phosphine oxide and a derivative thereof. In particular, it relates to a method of producing a bis(2-carboxyethyl)alkyl phosphine oxide and a derivative thereof, which is useful for imparting flame retardant properties and antistatic properties to fibers, plastics and the like.

Fibers, plastics, etc., are required to have high functionality such as flame retardant properties, resin modifying properties, and antistatic properties. For these uses, bis (carboxyethyl)methyl phosphine oxide derived from an organophosphorus compound such as methyl phosphine has been used. It has been disclosed that the polyester wherein this compound is co-polymerized shows good flame retardant properties (U.S. Pat. No. 4,127,566). This polyester copolymer, however, has such drawbacks as a large drop in melting point and somewhat low heat resistance.

In addition to that, methyl phosphine, which is to be used as raw material, is in gaseous form at ordinary temperature and ordinary pressure, and since it can easily ignite and explode when it is contacted with air, it is a very dangerous and hard-to handle substance, and it is very poisonous as well.

The compound of general formula (1), which is the compound according to the present invention, has been already disclosed in the production method of an organophosphorus compound (Japanese Patent Laid-Open Hei 6-166692, Japanese Patent Laid-Open Hei 6-166693) which is represented by the following general formula (4) as a raw material monomer for a flame-resistant polyester copolymer,

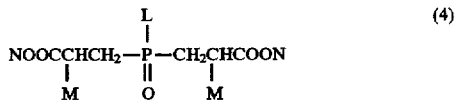

(wherein, L represents an alkyl group, aryl group, aralkyl group, or saturated alicyclic compound, M represents a hydrogen atom or an alkyl group having 1 to 4 carbon atoms, and N represents a hydrogen atom or methyl group.)

The production method comprises reaction of a primary phosphine with acrylonitrile, purification by distillation, oxidation with hydrogen peroxide, and hydrolysis with an alkali, however, monophenyl phosphine disclosed in the examples as an illustrative example of the primary phosphine, is hard to obtain and the price is high.

In view of above-mentioned facts, the present inventors carried out an intensive study of a bis(2-carboxyethyl)alkyl phosphine oxide as the functional organophosphorus compound, and found that a bis(2-carboxyethyl)alkyl phosphine oxide of the present invention can be produced with high purity and in high yields, by reacting phosphine with acrylonitrile, reacting the resulting product with an alkene, oxidizing the resulting product with an oxidizing agent, and carrying out hydrolysis or/and esterification, and completed the present invention. In addition to that, according to the method of the present invention, said compound can be economically produced by the use of a relatively inexpensive raw material, thus its industrial significance is great.

SUMMARY OF THE INVENTION

According to the present invention, there is provided a method of producing a bis(2-carboxyethyl)alkyl phosphine oxide represented by the following general formula (1), and a derivative thereof;

(wherein, $R^1$ represents a hydrogen atom, a straight or branched alkyl group, $R^2$ represents a hydrogen atom or methyl group, and $R^3$ represents a hydrogen atom and an alkyl group having 1 to 4 carbon atoms), which comprises the following Steps 1–4.

Step 1: a process wherein phosphine is reacted with acrylonitrile in the presence of an organic solvent and an alkali to produce bis(2-cyanoethyl)phosphine, Step 2: a process wherein said bis(2-cyanoethyl)phosphine is reacted with an alkene to produce a bis(2-cyanoethyl)alkyl phosphine represented by the following general formula (2), $$R^1-CHCH_2-P(CH_2CH_2CN)_2 \quad (2)$$
$$\overset{R^2}{|}$$

(wherein $R^1$ and $R^2$ have the same meanings as defined above),

Step 3: a process wherein said bis(2-cyanoethyl)alkyl phosphine is reacted with an oxidizing agent to produce a bis(2-cyanoethyl)alkyl phosphine oxide represented by the following general formula (3),

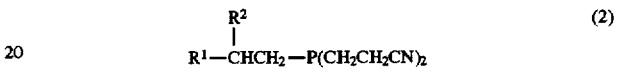

(wherein $R^1$ represents a hydrogen atom, a straight or branched alkyl group, $R^2$ represents a hydrogen atom or methyl group), Step 4: a process wherein said bis(2-cyanoethyl)alkyl phosphine oxide is reacted with water or a lower alcohol having 1 to 4 carbon atoms to give a bis(2-carboxethyl)alkyl phosphine oxide or a derivative thereof.

DETAILED DESCRIPTION OF THE INVENTION

The present invention will be described in detail. The method of producing a bis(2-carboxyethyl)alkyl phosphine oxide according to the present invention mainly comprises the following 4 steps.

STEP 1

Step 1 is a reaction process wherein phosphine is reacted with acrylonitrile in the presence of an organic solvent and an alkali to produce bis(2-cyanoethyl)phosphine.

The organic solvent is not particularly limited, and illustrative examples thereof include acetonitrile, dimethyl sulfoxide, methanol, and ethylene glycol, but a preferable example is acetonitrile.

Illustrative examples of the alkali include alkali metal salts such as potassium hydroxide, sodium hydroxide, and lithium hydroxide, but a preferable example is potassium hydroxide.

An appropriate molar ratio of phosphine to acrylonitrile is 2:1–1:3, preferably it is 1:1–1:2, more preferably it is 1:2. The amount of the organic solvent depends on the kind of the organic solvent, but illustratively it is 100–500 ml, preferably it is 200–300 ml for 1 mole of phosphine. The amount of the alkali metal salt is illustratively 0.1–1 mole, preferably 0.2–0.5 moles for 1 mole of phosphine.

The reaction is carried out under pressure using a high pressure vessel such as an autoclave.

The raw materials are charged in a reaction vessel after the reaction vessel is sufficiently purged with an inactive gas such as nitrogen or helium. An organic solvent and an aqueous alkali metal salt solution are charged first, and phosphine gas is introduced under pressure, then acrylonitrile is gradually introduced under pressure with stirring to carry out the reaction. The reaction temperature is normally −10° to 50° C., preferably 10° to 30° C. The reaction time is 1 to 10 hours, preferably 2 to 5 hours. The pressure depends on the reaction scale, but normally it is 10 to 20 kg/cm$^1$.

After the reaction is completed, maturation is carried out for 2 hours or more. After the maturation reaction is completed, the organic solvent layer and the aqueous alkali metal salt solution are separated according to the ordinary process. The product is obtained, being dissolved in the organic solvent layer. If necessary, it is washed with an aqueous sodium chloride solution to completely remove the remaining alkali.

STEP 2

Step 2 is a process wherein bis(2-cyaoethyl)phosphine obtained in the Step 1 is reacted with an alkene to produce a bis(2-cyanoethyl)alkyl phosphine.

Illustrative examples of the alkene include ethylene, propylene, 1-butene, 1-pentene, 1-hexene, 1-heptene, 1-octene, 1-nonene, 1-decene, cis-2-butene, trans-2-butene, isobutylene, 3-methyl-1-butene and the like.

The reaction in this process is carried out under an inactive atmosphere by adding an organic solvent and a reaction initiator and by applying pressure or under normal pressure, and the application of the pressure is decided by the nature of the alkene. For example, when an alkene which is in gaseous form at normal temperature, such as ethylene, propylene, 1-butene, isobutylene and 2-butene, is employed, the reaction is carried out under pressure.

The organic solvent is not particularly limited, and its illustrative examples include toluene, benzene, xylene, methanol, ethanol, n-hexane, n-pentane, isohexane, n-octane, n-isooctane, n-decane, petroleum ether, petroleum benzene, ligroin, petroleum spirit, petroleum naphtha, cyclohexane, methyl cyclohexane, methanol and ethanol, but preferable example include toluene, benzene, n-hexane and the like.

Illustrative examples of the reaction initiator include 1,1'-azobis(cyclohexane-1-carbonitrile), 2,2'-azobis(2-methylbutyronitrile), 2,2'-azobisisobutyronitrile, 2,2-azobis (2,4-dimethylvaleronitrile), 2,2'-azobis(4-methoxy-2,4-dimethlvaleronitrile), 4,4'-azobis(4-cyanovaleric acid), 2,2'-azobisdimethyl isobutyrate, 2,2'-azobis{2-methyl-N-[1,1-bis(hydroxymethyl)-2-hydroxyethyl]propionamide}, 2,2-azobis {2-methyl-N-[1,1-bis(hydroxymethyl) ethyl]propion amide}, 2,2 '-azobis[2-methyl-N-(2-hydroxyethyl) propionamide], 2,2'-azobis (2,4,4-trimethyl pentane), benzoyl peroxide, diisopropyl peroxy dicarbonate, t-butyl peroxy-2-ethyl hexanoate, t-butyl peroxy pivalate, t-butyl peroxy diisobutyrate, t-butyl peroxy isopropyl carbonate, lauroyl peroxide and the like.

In the above-mentioned reaction, an appropriate molar ratio of bis(2-cyanoethyl)phosphine to the alkene is 1:1–1:5, preferably it is 1:1–1:2.

The amount of the organic solvent is not necessarily limited, but illustratively it is 100–500 ml, preferably it is 200–300 ml for 1 mole of bis(2-cyanoethyl)phosphine, and similarly the amount of the reaction initiator is 0.1–10 moles, preferably 0.1–1 mole for 1 mole of bis(2-cyanoethyl)phosphine.

The reaction temperature is normally 50°–100° C., preferably 60°–80° C. The reaction time is normally 1–10 hours, preferably 2–5 hours. After the reaction is completed, if it is necessary, maturation is carried out.

STEP 3

Step 3 is a reaction process wherein the bis(2-cyanoethyl) alkyl phosphine obtained in the Step 2 is reacted with an oxidizing agent to produce the bis(2-cyanoethyl)alkyl phosphine oxide.

Illustrative examples of the oxidizing agent include peroxides such as hydrogen peroxide and benzoyl peroxide, nitrogen oxides such as nitric acid, NO, $N_2O_4$ and $N_2O$, as well as chlorine and the like, however, hydrogen peroxide is industrially advantageous.

The amount of the oxidizing agent varies according to the oxidizing agent, but an appropriate amount of the oxidizing agent is 1.0–1.1 moles, preferably 1–1.05 moles for 1 mole of the bis(2-cyanoethyl)alkyl phosphine.

An appropriate reaction temperature is room temperature −90° C., and it is preferable to carry out dropping reaction at 60°–70° C., followed by maturation reaction at the same temperature for 0.5–10 hours, preferably for 1–2 hours.

As for the reaction procedure, after the organic solvent and the bis(2-cyanoethyl)alkyl phosphine are charged, the oxidizing agent is added dropwise with stirring to carry out the reaction.

STEP 4

Step 4 is a reaction process wherein the bis(2-cyanoethyl) alkyl phosphine oxide obtained in the Step 3 is reacted with water or a lower alcohol having 1 to 4 carbon atoms to give the bis(2-carboxyethyl)alkyl phosphine oxide, which is the desired compound of the present invention.

Illustrative examples of the lower alcohol include methanol, ethanol, n-propanol, n-butanol and the like.

An appropriate amount of water or methanol is 2 moles or more, illustratively 2–50 moles, preferably 10–20 moles for 1 mole of the bis(2-cyanoethyl)alkyl phosphine oxide.

After the reaction is completed, the reaction mixture is concentrated to give the bis(2-carboxyethyl)alkyl phosphine oxide of the present invention as white crystal or colorless and transparent liquid.

Illustrative examples of the derivative of the bis(2-carboxyethyl)alkyl phosphine oxide of the present invention obtained by the above-mentioned reaction include a salt or an ester of the bis(2-carboxyethyl)alkyl phosphine oxide, such as bis(2-carboxyethyl)octyl phosphine oxide, bis(2-carboxyethyl)hexyl phosphine oxide, bis(2-carboxyethyl) butyl phosphine oxide, bis(2-carboxyethyl)ethyl phosphine oxide, bis(2-carboxyethyl)pentyl phosphine oxide, bis(2-carboxy-ethyl)nonyl phosphine oxide, bis(2-carboxyethyl) decyl phosphine oxide, bis(2-carboxyethyl)1-methyl propyl phosphine oxide, bis(2-carboxyethyl)2-methyl propyl phosphine oxide, bis(2-carboxyethyl)3-methyl butyl phosphine oxide, bis(2 -carbomethoxy ethyl)propyl phosphine oxide, bis(2-carbomethoxy ethyl)butyl phosphine oxide, bis(2-carbomethoxy ethyl)octyl phosphine oxide, bis(2-carbomethoxy ethyl)decyl phosphine oxide, bis(2-carbopropetoxy ethyl)ethyl phosphine oxide, bis(2-carbopropetoxy ethyl)propyl phosphine oxide, bis(2-carbopropetoxy ethyl)butyl phosphine oxide, bis(2-carbopropetoxy ethyl)octyl phosphine oxide, bis(2-carbopropetoxy ethyl)decyl phosphine oxide, bis(2-carbobutoxy ethyl)ethyl phosphine oxide, bis(2- carbobutoxy ethyl)propyl phosphine oxide, bis(2-carbobutoxy ethyl)butyl phosphine oxide, bis(2-carbobutoxy ethyl)octyl phosphine oxide, bis(2-carbobutoxy ethyl)decyl phosphine oxide and the like.

The production method of a derivative of a bis(2-carboxyethyl)alkyl phosphine oxide according to the present invention comprises four steps as described above, and it is mainly based on the following reaction formula.

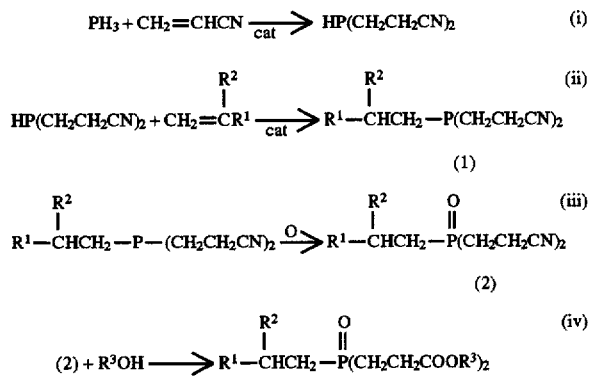

The reaction formula (i) represents bis(2-cyanoethyl) phosphine generation reaction in the Step 1 which is carried out in the presence of an alkali catalyst, the reaction formula (ii) represents addition reaction in the Step 2 wherein the phosphine product is reacted with an alkene in the presence of a catalyst. The reaction formula (iii) represents the reaction in the Step B wherein the addition product phosphine compound obtained according to the reaction formula (ii) is oxidized to give a phosphine oxide compound, and the reaction formula (iv) represents hydrolysis or esterification reaction in the Step 4. By employing those four reaction processes, a bis(2-carboxyethyl)alkyl phosphine oxide and a derivative thereof can be synthesized industrially advantageously.

In the production method according to the present invention, each step can be carried out continuously, however, in order to obtain a high purity product of a bis(2-carboxyethyl)alkyl phosphine oxide according to the present invention, (2-cyanoethyl)phosphine, tris(2-cyanoethyl)-phosphine or a derivative thereof produced in the Step 1 as impurity shall be removed in any of the steps by distillation purification.

The phosphorus compound according to the present invention contains two carboxy groups as shown in the above-mentioned general formula (3), thus it is bifunctional and shows homopolymerizability or copolymerizability with another monomer.

As the carbon and phosphorus in the functional group has P—C bond, the chemical and thermal stabilities of this compound are much better than other organophosphorus compounds having P—C bond (organophosphates).

EXAMPLES

To further illustrate the present invention, the following examples are given.

EXAMPLE 1

STEP 1

A stainless autoclave having a capacity of 1 liter was sufficiently purged with nitrogen, and 300 ml of acetonitrile and 50 ml of 10N potassium hydroxide aqueous solution were put in it. Then 34.0 g (1.0 mole) of phosphine was introduced from a bomb. Pressure gauge indicated 11.0 kg/cm$^2$. While cooling with water, 106.1 g (2.0 moles) of acrylonitrile was added gradually by a pressure pump for 3 hours, and the internal temperature was raised from 25° C. to 32° C. It was then matured for 2 hours. When the reaction was completed, the internal pressure was found to be equal to or less than 0.5 kg/cm$^2$. The system was purged with nitrogen several times and the reaction mixture was taken out.

The alkali aqueous solution, which was the lower layer of a separatory funnel, was separated and removed under nitrogen atmosphere, and the organic solvent layer was washed twice with 300 ml of saturated sodium chloride solution then dehydrated for twenty-four hours by anhydrous sodium sulfate. After the anhydrous sodium sulfate was removed, distillation was carried out under reduced pressure, and a fraction at 164°–165° C./1 mmHg was separated to give 102.5 g of a colorless transparent liquid. The relative purity analyzed by gas chromatography was 99.5% and the true yield based on phosphine was 72.8%.

The obtained liquid was analyzed by GC-MASS and confirmed to be bis(2-cyanoethyl)phosphine.

GC-MASS; m/z=140 (M$^+$)

STEP 2

Then a four-neck flask of 500 ml having a condenser, a thermometer, a dropping funnel and a stirrer was sufficiently purged with nitrogen, then 70.4 g (0.5 moles) of bis(2-cyanoethyl) phosphine obtained in the Step 1, 100 ml of toluene, 59.4 g (0.53 moles) of 1-octene were put in the flask. It was heated to 60° C. under nitrogen atmosphere and 0.75 g (3.0 millimoles) of 2,2'-azobis(2,4-dimethylvaleronitrile) dissolved in 50 ml of toluene was added dropwise for 3 hours. After the dropping was finished, it was matured at 60° C. for 1 hour. After cooling, excess 1-octene was removed by concentration under reduced pressure to give 130 g of a colorless and transparent viscous liquid (purity by nonaqueous titration of 93.3%, yield of 96.5%). The product was confirmed to be bis(2-cyanoethyl)octyl phosphine by FAB-MASS. FAB-MASS; m/z=253 (M+H)

STEP 3

A four-neck flask of 500 ml having a condenser, a thermometer, a dropping funnel and a stirrer was sufficiently purged with nitrogen, then 108.0 g (0.40 moles) of bis(2-cyanoethyl)octyl phosphine obtained in the Step 2, and 47.6 g (0.42 moles) of 30% hydrogen peroxide were gradually added dropwise so that the liquid temperature was kept at 60°–70° C., then it was further matured at 100° C. for 30 minutes.

After the reaction was completed, the reaction mixture was concentrated to give 112.4 g of a colorless and transparent liquid. It was confirmed to be bis(2-cyanoethyl)-octyl phosphine oxide by the measurement with FAB-MASS. FAB-MASS; m/z=269 (M+H)

STEP 4

Then 107.3 g of bis(2-cyanoethyl)octyl phosphine oxide obtained by the above-mentioned reaction and 100 ml of methanol were put in a four-neck flask of 500 ml having a condenser, a thermometer, a dropping funnel and a stirrer, and an aqueous potassium hydroxide solution, wherein 97.5 g (1.48 moles) of potassium hydroxide was dissolved in 100 ml of pure water, was gradually added at room temperature, and the temperature of the reaction mixture was raised to 45° C. It was refluxed for another 3 hours to carry out reaction.

The reaction mixture was concentrated to one-third of its volume, then the pH was controlled with concentrated hydrochloric acid to pH 4, and it was cooled to room temperature. The reaction mixture was separated into two layers, and the lower liquid was separated and concentrated to give 114.8 g of a slightly yellow solid. It was purified by recrystallization process from methanol and pure water to give 91.6 g of a white crystal. The product was confirmed to be bis(2-carboxyethyl)octyl phosphine oxide by FAB-MASS. The melting point was 95°–96° C. The purity of the product was 99.1% and the reaction yield was 80.2%.

FAB-MASS; m/z=307 (M+H)

EXAMPLE 2

In Step 1, a process analogous to that of Example 1 was carried out to give bis(2-cyanoethyl)phosphine as colorless and transparent liquid.

STEP 2

A four-neck flask of 500 ml having a condenser, a thermometer, a dropping funnel and a stirrer was sufficiently purged with nitrogen, then 70.4 g (0.5 moles) of bis(2-cyanoethyl) phosphine obtained in the Step 1, 100 ml of toluene, 44.5 g (0.53 moles) of 1-hexene were put in the flask. It was heated to 60° C. under nitrogen atmosphere and 0.60 g (2.4 millimoles) of 2,2'-azobis(2,4-dimethylvaleronitrile) dissolved in 50 ml of toluene was added dropwise for 3 hours. After the dropping was finished, it was matured at 60° C. for 1 hour. After cooling, excess 1-hexene was removed by concentration under reduced pressure to give 130.0 g of a colorless and transparent viscous liquid (purity by nonaqueous titration of 93.3%, yield of 96.5%). The product was confirmed to be bis(2-cyanoethyl)hexyl phosphine by FAB-MASS.

FAB-MASS; m/z=225 (M+H)

STEP 3

A four-neck flask of 500 ml having a condenser, a thermometer, a dropping funnel and a stirrer was sufficiently purged with nitrogen, then 95.0 g (0.40 moles) of bis(2-cyanoethyl)hexyl phosphine obtained in the above-mentioned reaction and 100 ml of toluene were put in it. 47.6 g (0.42 moles) of 30% hydrogen peroxide was gradually added dropwise so that the liquid temperature was kept at 60°–70° C. After the dropping was finished, it was matured at 100° C. for 30 minutes.

The reaction mixture was concentrated to give 98.1 g of a colorless and transparent liquid (purity by nonaqueous titration of 93.0%, yield of 95.0%). It was confirmed to be bis(2-cyanoethyl)hexyl phosphine oxide by the measurement with FAB-MASS.

FAB-MASS; m/z=241 (M+H)

STEP 4

Then 95.5 g (0.37 moles) of bis(2-cyanoethyl)hexyl phosphine oxide, 100 ml of pure water, 154.1 g (1.48 moles) of 35% concentrated hydrochloric acid were added to a four-neck flask of 500 ml having a condenser, a thermometer, a dropping funnel and a stirrer, and refluxed for 5 hours. After the concentration, the product was dissolved in 200 ml of acetone and precipitating ammonium chloride crystal was filtered out. The acetone solution was concentrated to give 105.8 g of a slightly yellow solid. It was purified by recrystallization from methanol and pure water to give 81.3 g of a white crystal. The product was confirmed to be bis(2-carboxyethyl)-hexyl phosphine oxide by the measurement with FAB-MASS. The melting point was 85°–86° C. The purity of the obtained product was 98.5% and the yield was 77.9%.

FAB-MASS; m/z=279 (M+H)

EXAMPLE 3

STEP 1

In Step 1, a process analogous to that of Example 1 was carried out to give bis(2-cyanoethyl)phosphine as colorless and transparent liquid.

STEP 2

70.4 g (0.5 moles) of bis(2-cyanoethyl)phosphine obtained in the Step 1, 100 ml of toluene, 33.7 g (0.60 moles) of 1-butene were put in a pressure resisting glass vessel of 300 ml which had been sufficiently purged with nitrogen. When the temperature was raised to 60° C., the internal pressure was found to be 1.8 kg/cm². 1.22 g (4.9 millimoles) of 2,2'-azobis(2,4-dimethylvaleronitrile) dissolved in 50 ml of toluene was added by a pressure pump for 3 hours and maturation was carried out at 60° C. for 2 hours. Since the pressure was found to be 0.2 kg/cm², it was cooled to room temperature.

The resulting reaction mixture was concentrated to give 94.8 g of a colorless and transparent viscous liquid (purity by nonaqueous titration of 93.1%, yield of 90.1%) and the product was confirmed to be bis(2-cyanoethyl)butyl phosphine by FAB-MASS.

FAB-MASS; m/z=108 (M+H)

STEP 3

A four-neck flask of 500 ml having a condenser, a thermometer, a dropping funnel and a stirrer was sufficiently purged with nitrogen then 80.0 g (0.38 moles) of bis(2-cyanoethyl)butyl phosphine obtained in the second reaction and 100 ml of toluene were put in it. 45.2 g (0.40 moles) of 30% hydrogen peroxide was gradually added dropwise so that the liquid temperature was kept at 60°–70° C., then it was matured at 100° C. for 30 minutes.

The reaction mixture was concentrated to give 86.5 g of a colorless and transparent liquid (purity by nonaqueous titration of 88.8%, yield of 95.3%), and it was confirmed to be bis(2-cyanoethyl)butyl phosphine oxide by the measurement with FAB-MASS.

FAB-MASS; m/z=213 (M+H)

STEP 4

Into a four-neck flask of 500 ml having a condenser, a thermometer, and a stirrer, were added 100 ml of pure water and 81.2 g (0.34 moles) of bis(2-cyanoethyl)butyl phosphine oxide, 141.6 g (1.36 moles) of 35% concentrated hydrochloric acid and refluxed for 5 hours.

The reaction mixture was concentrated, then dissolved in 200 ml of acetone and precipitating ammonium chloride crystal was filtered out. The acetone solution was concentrated to give 81.4 g of a slightly yellow solid. It was purified by recrystallization from methanol and pure water to give 64.2 g of a white crystal (purity of 97.9%, yield of 74.0%). The product was confirmed to be bis(2-carboxyethyl)butyl phosphine oxide by the measurement with FAB-MASS. The melting point was 132°–134° C.

FAB-MASS; m/z=251 (M+H)

EXAMPLE 4

STEP 1

In Step 1, a process analogous to that of Example 1 was carried out to give bis(2-cyanoethyl)phosphine as colorless and transparent liquid.

STEP 2

An acetonitrile solution containing bis(2-cyanoethyl) phosphine which had been obtained in the first reaction was put in a stainless autoclave of 1 liter, which had been purged with nitrogen. The internal temperature was raised to 60° C., and 42.1 g (1.5 moles) of ethylene was introduced under pressure from a bomb. The internal pressure was found to be 13.0 kg/cm$^2$. Then 4.97 g (20.0 millimoles) of 2,2'-azobis (2,4-dimethylvaleronitrile) dissolved in 100 ml of acetonitrile was added by a pressure pump for 3 hours and maturation was carried out at 60° C. for 2 hours.

Since the internal pressure was found to be reduced to 1.0 kg/cm$^2$, it was cooled to room temperature, the system was sufficiently purged with nitrogen and the reaction mixture was taken out.

Distillation under reduced pressure was carried out and a fraction at 169°–170° C./1.5 mmHg was separated to give 110.2 g of a colorless and transparent viscous liquid (purity by gas chromatography of 94.9%, yield of 62.2%), and it was confirmed to be bis(2-cyanoethyl)ethyl phosphine by GC-MASS.

GC-MASS; m/z=168 (M$^+$)

STEP 3

To a four-neck flask of 500 ml having a condenser, a thermometer, a dropping funnel and a stirrer, were added 88.5 g (0.5 moles) of bis(2-cyanoethyl)ethyl phosphine obtained in the third reaction and 100 ml of toluene. 60.1 g (0.53 moles) of 30% hydrogen peroxide was gradually added dropwise so that the liquid temperature was kept at 60°–70° C., then it was matured at 100° C. for 30 minutes.

The reaction mixture was concentrated to give 96.4 g of a colorless and transparent liquid (purity by nonaqueous titration of 89.4%, yield of 93.7%), and it was confirmed to be bis(2-cyanoethyl)ethyl phosphine oxide by the measurement with FAB-MASS.

FAB-MASS; m/z=186 (M+H)

STEP 4

Into a four-neck flask of 500 ml having a condenser, a thermometer and a stirrer, were added 100 ml of pure water, 102.9 g (0.5 moles) of bis(2-cyanoethyl)ethyl phosphine oxide and 208.3 g (2.0 moles) of 35% concentrated hydrochloric acid and refluxed for 5 hours. After the reaction mixture was completely concentrated by evaporator, it was dissolved in 100 ml of acetone and precipitating ammonium chloride crystal was filtered out. The acetone solution, which was the filtrate, was concentrated to give 81.8 g of a slightly yellow solid. It was purified by recrystallization from methanol and pure water to give 68.7 g of a white crystal (purity of 96.2%, yield of 59.5%). The product was confirmed to be bis(2-carboxyethyl)ethyl phosphine oxide by the measurement with FAB-MASS. The melting point was 114°–115° C.

FAB-MASS; m/z=223 (M+H)

EXAMPLE 5

STEP 1–STEP 3

From Step 1 through Step 3, processes analogous to those of Example 4 were carried out to give bis(2-cyanoethyl) ethyl phosphine oxide.

STEP 4

Into a four-neck flask of 1 liter, having a condenser, a thermometer and a stirrer, were added 100.9 g (0.5 moles) of bis(2-cyanoethyl)ethyl phosphine oxide obtained in the above-mentioned third reaction, 250 ml of methanol and 200 g (2.0 moles) of concentrated sulfuric acid. It was recognized that heat was generated by adding sulfuric acid, then methanol was refluxed for another 8 hours. After cooling, 200 ml of pure waster was added and extraction with 300 ml of dichloromethane was carried out. The extracted layer was washed with 10% sodium carbonate aqueous solution and dehydrated with anhydrous sodium sulfate for 24 hours.

After concentration, it was distilled under reduced pressure and a fraction at 188°–191° C./2.5 mmHg was separated to give 106.0 g of a colorless and transparent liquid (purity of 96.4%, yield of 82.2%). The product was confirmed to be bis(2-carboxymethoxyethyl)ethyl phosphine oxide by the measurement with GC-MASS.

GC-MASS; m/z=250 (M$^+$)

According to the present invention, there is provided a method of producing a bifunctional alkyl phosphine oxide which is useful for imparting flame retardant properties, antistatic properties and the like to fibers or plastics.

According to the production method of the present invention, all the raw materials are inexpensive, the product can be supplied with an economical price, thus its economic effect is big and the industrial significance is great.

This useful organophosphorus compound has been used in a wide variety of fields including as flame retardants, antistatic additives, antibacterial agents, dyeing improving agents, resin modifiers, stain-proofing agents, and rust preventives.

What is claimed is:

1. A method of producing a bis(2-carboxyethyl)-alkyl phosphine oxide represented by the following general formula (1), and a derivative thereof;

$$R^1-\text{CHCH}_3-\overset{\overset{\displaystyle R^2}{|}}{\underset{\underset{\displaystyle}{}}{P}}(\text{CH}_2\text{CH}_2\text{COOR}^3)_2 \quad \overset{O}{\|} \tag{1}$$

(wherein, $R^1$ represents a hydrogen atom, a straight or branched alkyl group, $R^2$ represents hydrogen atom or methyl group, and $R^3$ represents a hydrogen atom and an alkyl group having 1 to 4 carbon atoms), which comprises the following Steps 1–4;

Step 1: reacting phosphine with acrylonitrile in the presence of an organic solvent and an alkali to produce bis(2-cyanoethyl)phosphine, Step 2: reacting said bis(2-cyanoethyl)phosphine with an alkene to produce a bis(2-cyanoethyl)alkyl phosphine represented by the following general formula (2), $$R^1-\text{CHCH}_2-\overset{\overset{\displaystyle R^2}{|}}{P}(\text{CH}_2\text{CH}_2\text{CN})_2 \tag{2}$$

(wherein $R^1$ and $R^2$ have the same meanings as defined above),

Step 3: reacting said bis(2-cyanoethyl)alkyl phosphine with an oxidizing agent to produce a bis(2-cyanoethyl)alkyl phosphine oxide represented by the following general formula (3),

  (3)

(wherein $R^1$ and $R^2$ have the same meanings as defined above),

Step 4: reacting said bis(2-cyanoethyl)alkyl phosphine oxide with water or a lower alcohol having 1 to 4 carbon atoms to give a bis(2-carboxyethyl)alkyl phosphine oxide or a derivative thereof.

2. A method according to claim 1, wherein the molar ratio of phosphine to acrylonitrile in the Step 1 is 2:1–1:3.

3. A method according to claim 1 or claim 2, wherein the molar ratio of bis(2-cyanoethyl)phosphine to an alkene in the Step 2 is 1:1–1:2.

4. A method according to one claim 1, wherein hydrogen peroxide is used as the oxidizing agent in the Step 3.

5. A method according to claim 1, wherein (2-cyanoethyl)phosphine, tris(2-cyanoethyl)phosphine or a derivative thereof which is produced as an impurity in the Step 1, is removed in any of the subsequent Steps.

6. A method according to claim 2, wherein hydrogen peroxide is used as the oxidizing agent in the Step 3.

7. A method according to claim 2, wherein (2-cyanoethyl)phosphine, tris(2-cyanoethyl)phosphine or a derivative thereof which is produced as an impurity in the Step 1, is removed in any of the subsequent Steps.

8. A method according to claim 4, wherein (2-cyanoethyl)phosphine, tris(2-cyanoethyl)phosphine or a derivative thereof which is produced as an impurity in the Step 1, is removed in any of the subsequent steps.

9. A method according to claim 6, wherein (2-cyanoethyl)phosphine, tris(2-cyanoethyl)phosphine or a derivative thereof which is produced as an impurity in the Step 1, is removed in any of the subsequent steps.

* * * * *